United States Patent [19]

Kosaka

[11] Patent Number: 5,159,403
[45] Date of Patent: Oct. 27, 1992

[54] FLOW CELL MECHANISM IN FLOW IMAGING CYTOMETER

[75] Inventor: Tokihiro Kosaka, Hyogo, Japan

[73] Assignee: TOA Medical Electronics Co., Ltd., Kobe, Japan

[21] Appl. No.: 671,531

[22] Filed: Mar. 19, 1991

[30] Foreign Application Priority Data

Nov. 22, 1990 [JP] Japan .................................. 1-319152

[51] Int. Cl.⁵ .......................................... G01N 21/00
[52] U.S. Cl. ................................ 356/243; 250/201.2; 356/73
[58] Field of Search ............... 356/73, 243; 250/201.2, 250/201.3, 201.7, 252.1

[56] References Cited

U.S. PATENT DOCUMENTS

| | | | |
|---|---|---|---|
| 4,519,087 | 5/1985 | Deindoerfer | 377/10 |
| 4,690,561 | 9/1987 | Ito | 356/73 |
| 4,715,708 | 12/1987 | Ito | 356/73 |
| 4,732,479 | 3/1988 | Tanaka et al. | 356/336 |

Primary Examiner—Richard A. Rosenberger
Attorney, Agent, or Firm—Pearne, Gordon, McCoy & Granger

[57] ABSTRACT

A flow imaging cytomer for imaging the dimensions and shapes of particle components in a flow of a specimen solution has a slender filament serving as a focusing reference provided in a flat imaging zone through which the specimen solution flows in order for the particle components to be imaged. By imaging the filament-shaped focusing reference and adjusting position in accordance with the sharpness of an image of the reference, the particle components in the specimen solution can be brought into sharp focus.

12 Claims, 1 Drawing Sheet

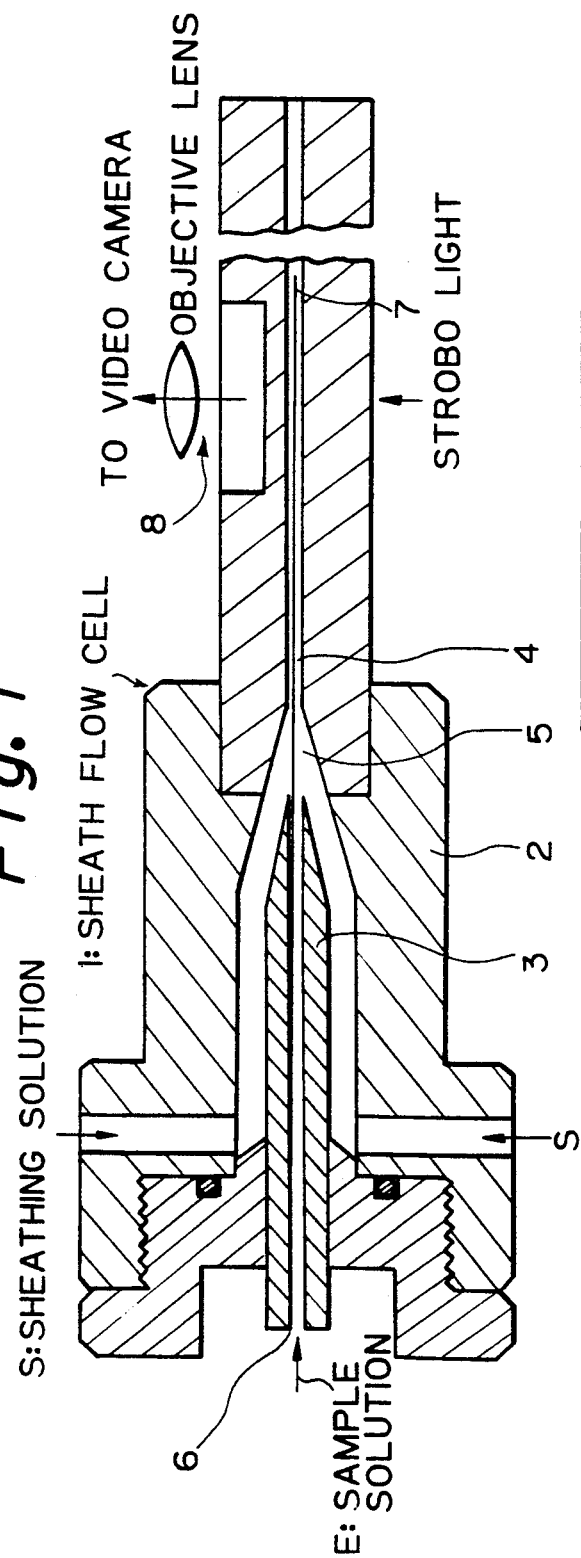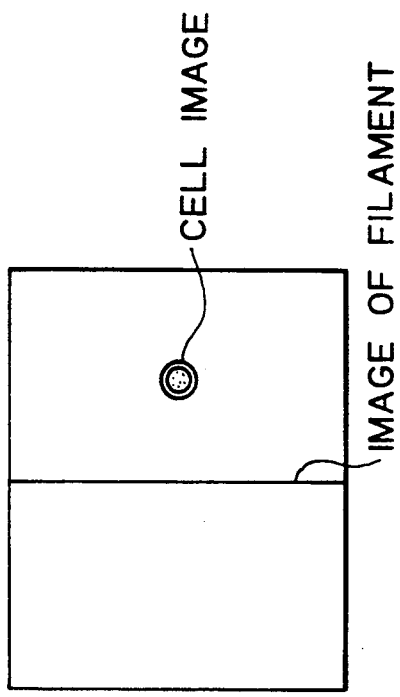

FLOW CELL MECHANISM IN FLOW IMAGING CYTOMETER

BACKGROUND OF THE INVENTION

1. Field of the Invention

This invention relates to autofocusing in a system in which a specimen such as blood or urine suitably stained is introduced to a flow cell to form a flat, sheathed flow within the cell, the sheathed flow zone is irradiated with strobe light, and a cell image obtained by a video camera is analyzed by application of image processing. More particularly, the invention relates to a flow cell mechanism in a flow imaging cytometer in which a slender filament is passed through a sampling nozzle within the flow cell, the state of focus of an image of the filament is monitored at all times by the apparatus itself and the position of the flow cell or lens is moved finely in automatic fashion when the image of the filament is out of focus, thereby making it possible to readjust focus automatically.

2. Description of the Prior Art

In an image processing system for imaging cells which flow through a flow cell and applying prescribed image processing, an image in which the cells appear at rest by illuminating them with strobe light is obtained. Such an image, which is obtained frame by frame (i.e., every 1/30 of a second), differs from that of the immediately preceding frame. In a still camera or domestic video camera, there is almost no movement of the image from one frame to the next, and therefore focusing of the type in which camera lens is moved in fine increments is comparatively easy to perform. However, in a case where the image changes every frame, focus cannot be adjusted by comparing identical images with each other while subjecting the flow cell or lens to fine movement. Even if a focal adjustment in such case is performed manually while viewing the image, it is difficult to judge whether focus is perfect and it takes 5 minutes or more to adjust. Moreover, since the optical system can experience some slippage owing to changes in ambient temperature, re-focusing is required often.

In order to prevent defocusing due to changes in temperature, the apparatus should be controlled so as to hold the overall optical system at a constant temperature. However, such control means raises the cost of the apparatus.

A different expedient is to adopt a method in which the user measures a control fluid, which is employed in order to control the accuracy of the apparatus, after which the apparatus itself performs focusing while finely moving the flow cell or lens based upon the images of particles whose sizes are uniform within the control fluid. However, in order to correctly obtain an evaluation value indicative of whether or not focusing has been achieved in a case where only a small number of cells appear in a single imaged frame, it is necessary to derive the evaluation value from data indicative of imaged frames consisting of several dozen frames. Consequently, considerable time is required to perform an adjustment while comparing evaluation values from point to point during the fine movement of the flow cell or lens. In addition, this method necessitates not only the reagent but also labor on the part of the user, who is required to measure the control fluid.

SUMMARY OF THE INVENTION

An object of the present invention is to provide a novel flow cell mechanism, as well as a focal-point adjustment method in cytometry, which solves the aforementioned problems encountered in the prior art.

According to the present invention, the foregoing object is attained by providing a flow cell mechanism in a flow imaging cytometer of the type in which a specimen solution containing particle components such as cells is made to flow, while sheathed by a sheathing liquid, through an imaging zone of a flat flow path within a flow cell, a still image of the specimen solution flow is photographed in the imaging zone by light irradiating means and imaging means so arranged that an optic axis thereof intersects the flow path, and the still image is subjected to image processing, whereby analysis such as classification and enumeration of the particle components contained in the specimen solution is performed, characterized in that a focusing reference for focus adjustment is provided in the zone through which the specimen solution flows and is photographed.

Further, the foregoing object is attained by providing an automatic focal-point adjustment method in flow imaging cytometry of the type in which a specimen solution containing particle components such as cells is formed into a flat, laminar flow sheathed by a sheathing liquid, a still image of the specimen solution flow is photographed in a flow zone and the still image is subjected to image processing, whereby analysis such as classification and enumeration of the particle components contained in the specimen solution is performed, characterized by imaging a filament-shaped body as a focusing reference for focus adjustment provided in the flow zone, and adjusting position in accordance with clarity of an image of the filament-shaped body, thereby performing a focus adjustment with regard to the particle components in the specimen solution.

Other features and advantages of the present invention will be apparent from the following description taken in conjunction with the accompanying drawings.

BRIEF DESCRIPTION OF THE DRAWINGS

FIG. 1 is a longitudinal sectional view illustrating an embodiment of a flow cell mechanism in a cytometer according to the present invention; and FIG. 2 is a diagram showing an example of an image in which both a filament and a cell particle contained in a specimen solution reside.

DESCRIPTION OF THE PREFERRED EMBODIMENT

An embodiment of the present invention will now be described in detail with reference to the accompanying drawings.

As shown in FIGS. 1 and 2, a sheath flow cell 1 has a cell body 2 accommodating a sampling nozzle 3 the rear end of which has a fixing portion 6 for fixing the rear end of a slender filament 5 having a free end 7 passed through the interior of the nozzles 3, the diameter whereof is on the order of several microns (e.g., 2-5 $\mu$m). A sheathing solution S is admitted into the cell body 2 to sheath a sample solution E that flows through a flat flow path 4. The arrangement is such that the filament 5 will flow along with the particles in the sample solution E as it flows by an imaging zone 8 of a video camera. This makes it possible to always pick up the image of the filament 5 at a position substantially fixed in the imaged frame every 1/30 of a second. In addition, if the filament 5 is in focus, then so will be the image of the cell. Rather than concentrating on the images of cells of an indeterminate number appearing at different positions in the imaged frame from one instant to the next, as is done in the prior art, operation according to the invention is simpler and can be performed in a shorter period of time by evaluating focusing based upon the image of the single, substantially unmoving slender filament 5.

An example of an evaluation as to whether an image is in focus is as described in the specification of Japanese Patent Application No. 2-195934. As applied to this invention, quadratic differential values (referred to as a Sobel values or Laplacian values) of the image data are accumulated over the zone in which the filament 5 appears. The value obtained by such accumulation can be used in making an evaluation of focus. Values can be obtained in real-time (every 1/30 of a second) by using an ordinary real-time 3×3 convolution circuit as the image processing circuit employed in making the evaluation. In such case, the focal adjustment would be performed in real-time with regard to the imaged frame every 1/30 of a second while minutely moving the flow cell or lens.

Example of materials usable as the filament 5 are metallic fibers, chemically synthesized fibers, ceramic fibers and the like. In any case, use should be made of a strongly corrosion-resistant, highly rigid material which will not bend.

With the arrangement of the present invention described above, a change in the relative positions of the specimen solution and optical system will result in loss of focus and cause blurring of the particle image. However, since the focusing reference for focal adjustment (namely the filament 5 in the illustrated preferred embodiment) is provided in the zone through which the specimen solution flows, the particle components in the specimen solution can be restored to sharp focus by bringing the focusing reference into focus.

If the focusing reference adopted is the filament 5, as described and illustrated above, the reference will flow smoothly along with the specimen solution.

In a case where the filament 5 is passed through the sampling nozzle 1 and disposed in the flat flow path 4 of the flow cell, the center of the specimen stream will drift more stably and the filament 5 therefore will virtually be fixed in position.

The image of the filament 5 for focal adjustment purposes is used in a positional adjustment performed by a focal-point adjusting mechanism in accordance with the clarity of the image.

Thus, a flow imaging cytometer according to the present invention provides the following effects:
(1) The apparatus itself is capable of monitoring the status of focus at all time, and therefore focusing can be performed without the intervention of the user.
(2) It is unnecessary to use special particles of a uniform size and shape for the purpose of adjusting focus. This makes it possible to reduce management cost.
(3) The time required for focus adjustment according to the invention is less than that entailed by the method using the aforementioned special particles for adjustment.
(4) A focused image is obtained in which focusing is stable at all times despite changes in ambient temperature.

As many apparently widely different embodiments of the present invention can be made without departing from the spirit and scope thereof, it is to be understood that the invention is not limited to the specific embodiments thereof except as defined in the appended claims.

What is claimed is:

1. In a flow imaging cytometer in which a specimen solution containing particle components such as cells is made to flow, while sheathed by a sheathing liquid, through a flat flow path within a flow cell, a still image of the specimen solution flow is photographed by light irradiating means and imaging means so arranged that an optic axis thereof intersects the flow path, and the still image is subjected to image processing, whereby analysis such as classification and enumeration of the particle components contained in the specimen solution is performed, a flow cell mechanism which includes:
   a focusing reference for focus adjustment comprising an element suspended within the zone through which the specimen solution flows and is photographed.

2. The flow cell mechanism according to claim 1, wherein said focusing reference element is a filament-shaped body.

3. The flow cell mechanism according to claim 2, wherein said filament-shaped body is suspended in and extends longitudinally through said flat flow path and further extends through a sampling nozzle of the flow cell.

4. The flow cell mechanism according to claim 3, wherein said filament-shaped body has a diameter of 2-5 $\mu$m.

5. The flow cell mechanism according to claim 4, further comprising focal-point adjusting means for adjusting the relative position of said flow cell and said imaging system in correlation with sharpness of the image of said focusing reference when said focusing reference is imaged.

6. The flow cell mechanism according to claim 3, further comprising focal-point adjusting means for adjusting the relative position of said flow cell and said imaging system in correlation with sharpness of the image of said focusing reference when said focusing reference is imaged.

7. The flow cell mechanism according to claim 2, further comprising focal-point adjusting means for adjusting the relative position of said flow cell and said imaging system in correlation with sharpness of the image of said focusing reference when said focusing reference is imaged.

8. The flow cell mechanism according to claim 1, further comprising focal-point adjusting means for adjusting the relative position of said imaging means and said flow cell in correlation with sharpness of the image of said focusing reference when said focusing reference is imaged.

9. In flow imaging cytometry in which a specimen solution containing particle components such as cells is formed into a flat, laminar flow sheathed by a sheathing liquid, a still image of the specimen solution flow is photographed in a flow zone and the still image is subjected to image processing, whereby analysis such as classification and enumeration of the particle components contained in the specimen solution is performed, an automatic focal-point adjustment method comprising the steps of:

imaging a filament-shaped body as a focusing reference for focus adjustment provided in the flow zone; and adjusting position in accordance with sharpness of an image of said filament-shaped body, thereby performing a focus adjustment with regard to the particle components in the specimen solution.

10. the focal-point adjustment method according to claim 9, further comprising a step of continuously imaging said filament-shaped body while making fine adjustments in relative positions of the flow cell and a lens system.

11. The focal-point adjustment method according to claim 10, further comprising the steps of:

continuously monitoring state of focus in accordance with said sharpness of the image, and adjusting the relative position of said flow cell and said imaging system when the state of focus is indicative of a value less than a predetermined value.

12. The focal-point adjustment method according to claim 9, further comprising the steps of:

continuously monitoring the state of focus in accordance with said sharpness of the image; and adjusting the relative position of said flow cell and said imaging system when the state of focus is indicative of a value less than a predetermined value.

* * * * *